(12) United States Patent
AlSaffar

(10) Patent No.: US 8,998,833 B1
(45) Date of Patent: Apr. 7, 2015

(54) ORTHOPEDIC DEVICE AND METHOD FOR CORRECTING SKELETAL ABNORMALITIES IN A NEW-BORN BABY

(71) Applicant: Abdulreidha Abdulrasoul AlSaffar, Sharg (KW)

(72) Inventor: Abdulreidha Abdulrasoul AlSaffar, Sharg (KW)

( * ) Notice: Subject to any disclaimer, the term of this patent is extended or adjusted under 35 U.S.C. 154(b) by 0 days.

(21) Appl. No.: 14/178,676

(22) Filed: Feb. 12, 2014

(51) Int. Cl.
*A61F 5/00* (2006.01)
*A61F 5/01* (2006.01)

(52) U.S. Cl.
CPC ..................................... *A61F 5/013* (2013.01)

(58) Field of Classification Search
USPC .......... 602/22, 5, 20, 16, 21, 60–64; D24/190–192; 473/61–63; 2/161.1, 2/162, 16; 482/44, 45, 46, 47, 49
See application file for complete search history.

(56) References Cited

U.S. PATENT DOCUMENTS

| | | |
|---|---|---|
| 3,049,120 A | 8/1962 | Marcus |
| 4,088,129 A | 5/1978 | DiGiulio |
| 4,180,870 A | 1/1980 | Radulovic et al. |
| 4,244,359 A | 1/1981 | Dieterich |
| 4,320,747 A | 3/1982 | Daniell, Jr. |
| 4,608,970 A | 9/1986 | Marck et al. |
| 4,649,906 A | 3/1987 | Spademan |
| 5,002,044 A | 3/1991 | Carter |
| 5,183,036 A | 2/1993 | Spademan |
| 5,308,312 A | 5/1994 | Pomatto et al. |
| 5,385,536 A | 1/1995 | Burkhead et al. |
| 5,421,810 A | 6/1995 | Davis et al. |
| 5,503,621 A | 4/1996 | Miller |
| 5,538,499 A | 7/1996 | Schwenn et al. |
| 5,662,595 A * | 9/1997 | Chesher et al. .................. 602/20 |
| 6,533,741 B1 | 3/2003 | Lee et al. |
| 7,083,583 B2 | 8/2006 | Opahle et al. |
| 7,402,148 B2 * | 7/2008 | Brewer ........................... 602/21 |
| 7,841,998 B2 | 11/2010 | Pomeroy et al. |
| 7,988,652 B2 | 8/2011 | Chao |
| 8,251,934 B2 | 8/2012 | Bonutti |
| 2012/0330204 A1 | 12/2012 | Baldauf et al. |

* cited by examiner

*Primary Examiner* — Kim M Lewis
(74) *Attorney, Agent, or Firm* — Lowe Hauptman & Ham, LLP

(57) ABSTRACT

An orthopedic device for correcting abnormalities in the wrist, hand, fingers and thumb of a newborn baby comprises a lightweight glove shaped semi rigid shell constructed and dimensioned to fit a newborn baby within a few hours of birth. A wrist or lower arm and hand engaging portion are rotatably connected and adjustable in one millimeter increments. The adjustments are made with no more than one millimeter correction per 24 hour period. The shell includes a wrist and lower forearm engaging portion, a hand engaging portion and a finger engaging portion and is adjustable for rotationally clockwise or counterclockwise about the longitudinal axis of the lower arm bone. Further adjustments may be made to rotate the fingers upwardly or downwardly, to the left or right and rotationally and/or rotational movement between the hand and lower arm. The invention also contemplates an orthopedic method for correcting skeletal abnormalities of the wrist, hand, fingers and thumb of a newborn baby.

6 Claims, 6 Drawing Sheets

ORTHOPEDIC DEVICE AND METHOD FOR CORRECTING SKELETAL ABNORMALITIES IN A NEW-BORN BABY

FIELD OF THE INVENTION

This invention relates to an orthopedic device and method for correcting skeletal abnormalities in a new-born human baby and more particularly to a device and method for correcting abnormalities in the wrist, hand, fingers and thumb of a newborn human baby within a few or slightly more hours of birth.

BACKGROUND FOR THE INVENTION

Some babies are born with skeletal abnormalities as for example in the hands, feet and in other important parts of the body such as a patient's shoulders, arms, legs, hands, fingers and thumb, their neck, legs and knees. My co-pending U.S. Patent Application filed on even date herewith Ser. No. 14/178,443, is entitled "Orthotic Methods and Devices for Newborn Babies" and relates more specifically to orthopedic devices for correcting abnormalities in the feet and toes of a newborn human baby.

Correction of skeletal abnormalities of important parts of a human body of young children have been done for many years. For example, a U.S. Pat. No. 5,002,044 issued to Carter discloses a derotation wrist brace. As disclosed therein a derotation wrist brace provides volar reduction force and allows early movement of the radiocarpal joint. A first pair of struts are attached to a forearm support member at their first ends. The second ends of the first struts are attached to a first rotation plate. A second pair of struts are attached to a hand support member at their first ends. The second ends of the second struts are attached to a second rotation plate. The first rotation plates and the second rotation plates are coaxially mounted on a pair of shafts.

A more recent U.S. Pat. No. 7,841,998 of Pomeroy et al. discloses a non-invasive external fixator particularly suitable for fracture fixation. In particular, the fixator of the invention includes proximal and distal portions for mounting on a limb either side of a fracture. Each of the proximal and distal portions includes a rigid member. An articulation member connects the proximal and distal portions and includes a universal joint for allowing relative movement between the proximal and distal portions wherein the articulation member connects the rigid members.

Notwithstanding the above, it is presently believed that there is a need and a potential commercial market for an orthopedic device for correcting abnormalities in a newborn baby within several hours of the baby's birth. There should be a need because the devices in accordance with the present invention provide early remedy to correct such abnormalities and does so in a painless and efficient manner.

BRIEF SUMMARY OF THE INVENTION

In essence the present invention contemplates an orthopedic device for correcting abnormalities in the wrist, hand, fingers and thumb of a newborn baby within one (1) to ten (10) hours of the baby's birth. In a preferred embodiment of the invention, the device comprises and/or consists of a lightweight glove shaped shell constructed and dimensioned to fit over the wrist, hand and a portion of the fingers and thumb of the newborn infant.

The shell includes a wrist and lower forearm engaging portions, a hand engaging portion rotatably connected to the wrist and lower arm portion for rotation upwards and downwards, to the right and to the left and rotatable clockwise or counterclockwise about the longitudinal axis of the lower arm bone.

In addition, the device includes one or more adjustment mechanisms for adjusting the rotational movement between the wrist and lower arm portion and the hand portion in one millimeter (mm) increments.

The invention also contemplates an orthopedic method for correcting skeletal abnormalities in the wrist, hand, fingers and thumb of a newborn human baby. The method comprises and/or consists of the following steps.

In a first step a newborn baby is given a physical examination by a medical or orthopedic professional for skeletal abnormalities of the wrist, hands, fingers and thumb. Then, if one or more abnormalities are found a next step includes providing a lightweight glove shaped shell like member constructed and dimensioned to fit a newborn baby's wrist, hand, fingers and/or thumb inclusive of the abnormality. The glove shaped member includes an adjustment mechanism for adjusting the rotational movement between the wrist and hand up and downward, right or left and clockwise or counterclockwise about the longitudinal axis of the lower arm bone. In the next step the adjustment mechanism biases the movement by about one (1) millimeter (mm) and is allowed to remain in that position for about 24 hours and subsequently adjusted in one (1) millimeter increments per 24 hour period until a normal position is reached and stabilized.

The device and method will now be described in connection with the accompanying drawings wherein like parts are designated with like numbers.

DETAILED DESCRIPTION OF THE PREFERRED EMBODIMENTS OF THE INVENTION

Figure 1:
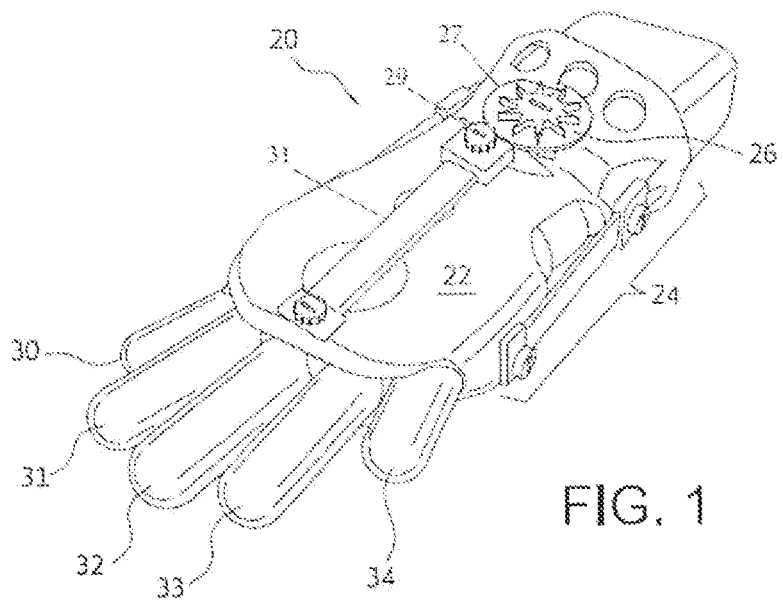
FIG. 1 is a perspective view of an orthopedic device for correcting abnormalities in the wrist, hand, fingers and thumb of a newborn baby in accordance with a first preferred embodiment of the invention.
Figure 2:
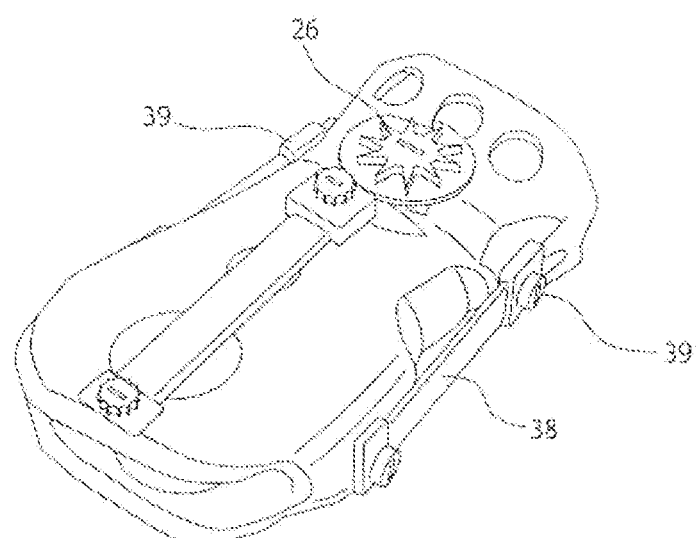
FIG. 2 is a perspective view of a shell member as used in the orthopedic device shown in FIG. 1.
Figure 3:
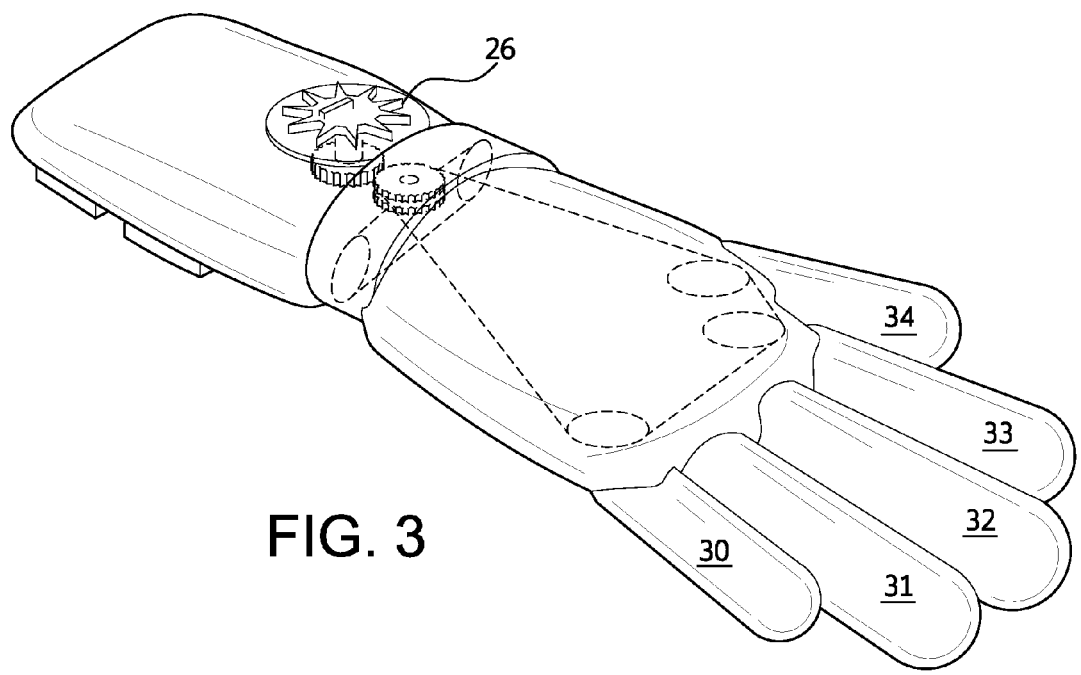
FIG. 3 is a perspective view of an orthopedic device as illustrated in FIG. 1 with the shell member illustrated in FIG. 2 removed.
Figure 12:
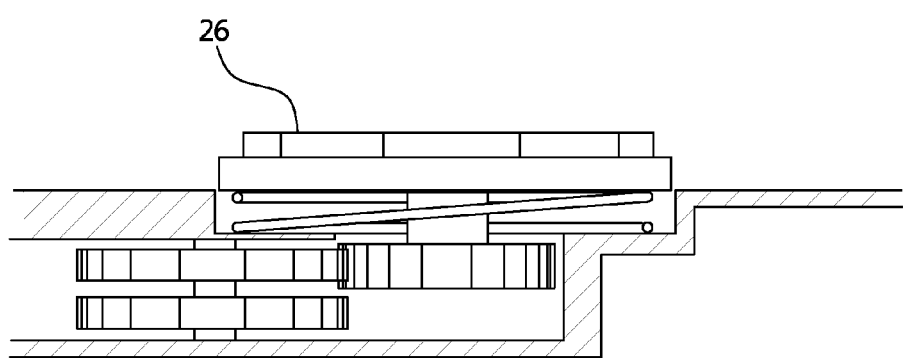
FIG. 12 is a schematic illustration of an adjustment mechanism for biasing the wrist, hand, fingers and thumb towards a correct or normal position.

As illustrated in FIGS. 1 and 3, an orthopaedic device 20 includes a very lightweight generally glove shaped shell 22 that is constructed and dimensioned to cover and engage a very small new-born human baby's hand within a few hours of the baby's birth. For example, the gloved shaped shell fits over the baby's finger and thumb, hand and wrist and may be one part or multiple parts. As illustrated in FIG. 2, the shell slides over the fingers and thumb and wrist and lower portion of a new-born baby's lower arm bone. In a preferred form the device includes a hand and wrist engaging member 24 and an adjustment mechanism 26. The adjustment mechanism 26 is illustrated by a dial that moves in a clockwise or counter clockwise direction and may have two positions namely an upward position and downward position for controlling different portions of the device. The adjustment mechanism includes a planar gear 27 disposed on the glove shaped shell 22 engaging a gear 29 of a slidable member 31. The adjustment mechanism also includes a pair of opposing adjustment bars 38 supported at their opposing ends by support members 39.

As illustrated in FIGS. 1, 3, 4 and 5, the device 20 includes five separate compartments 30, 31, 32, 33 and 34, four compartments 30-33 one for each of the four fingers and a fifth compartment 34 for the patient's thumb. In a preferred embodiment the fingers are moved as a unit to the left or right and/or up or down.

Figure 4:
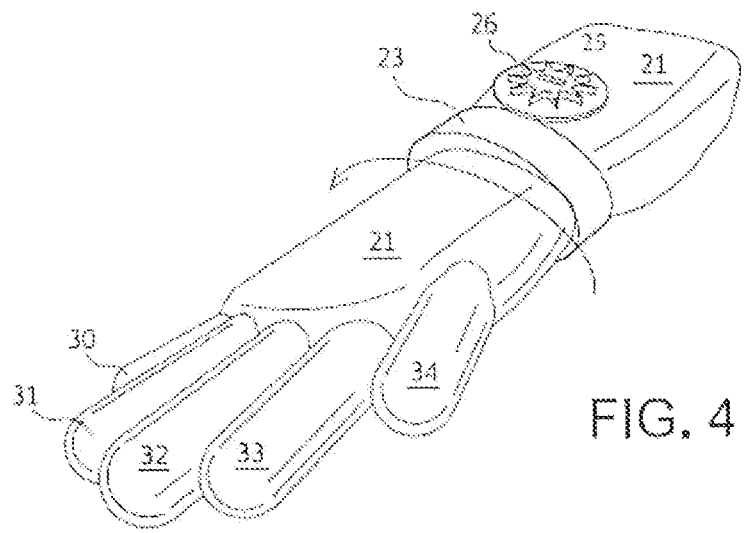
FIG. 4 is a perspective view of the orthopedic device as shown in FIG. 3 but with the hand and fingers as a unit rotated counterclockwise with respect to the longitudinal axis of the lower arm.
Figure 5:
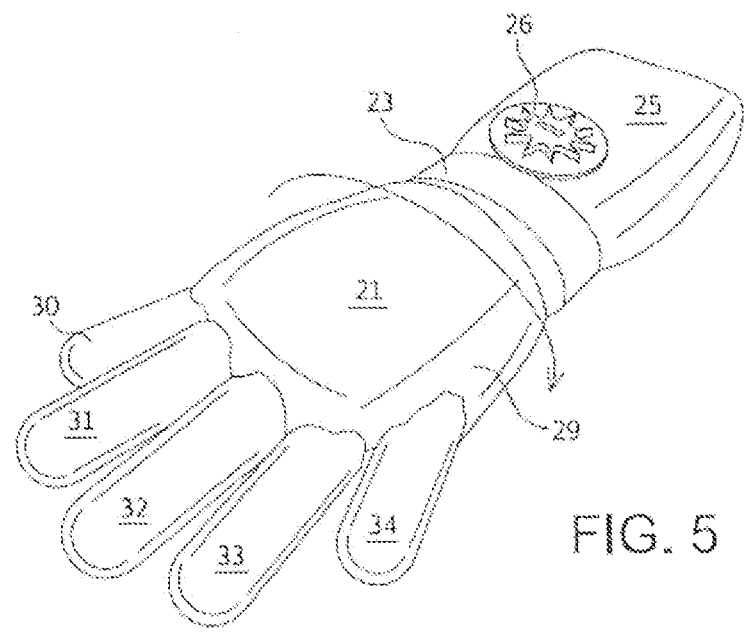
FIG. 5 is a perspective view of the orthopedic device as shown in FIG. 4 but with the hand rotated clockwise with respect to the longitudinal axis of the lower arm bone.

FIGS. 3, 4 and 5 illustrate a modified device or second embodiment of the invention wherein a hand engaging portion 21, wrist engaging portion 23 and lower arm engaging portion 25 are connected together. However, the wrist engaging portion 23 allows for sufficient flexibility to rotate the hand engaging portion 21 to be rotated to a limited degree about a longitudinal axis of the patient's lower arm bone. The rotation can be in a clockwise or counterclockwise manner as illustrated in FIGS. 4 and 5.

Figure 6:
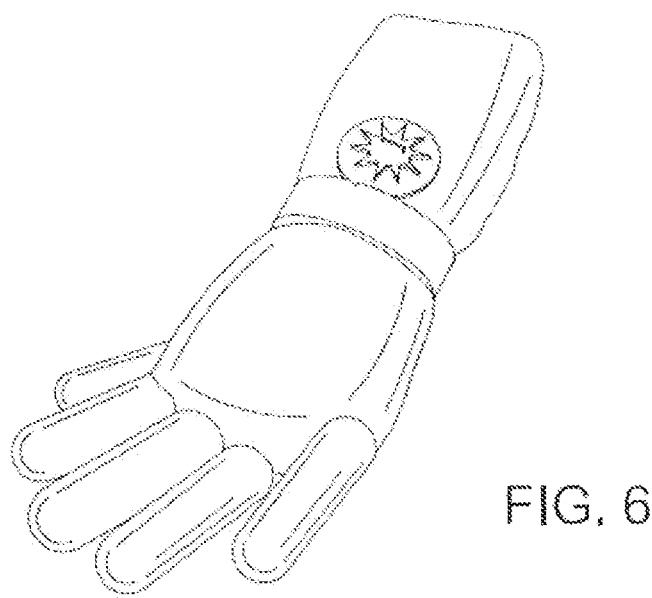
FIG. 6 is a perspective view of the orthopedic device as shown in FIGS. 1 through 5 with an abnormality of the fingers in the right direction before correction.
Figure 7:
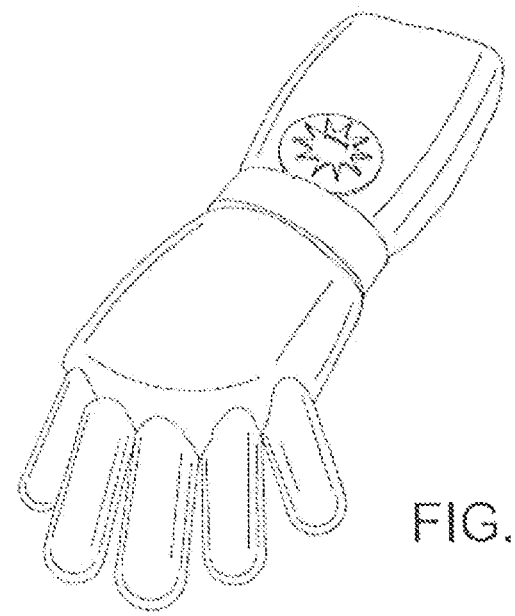
FIG. 7 is a perspective view of the orthopedic device as shown in FIG. 3 with the fingers oriented to the left prior to correction.

FIGS. 6 and 7 illustrate movement of the fingers and thumb from a right or left orientation due to an abnormality to a central or normal position. Under such circumstances, the fingers and thumb compartments are oriented to receive the fingers and thumb of a newborn patient and the orientation is moved in one (1) mm increments toward a normal or central position. To be more specific, the fingers are biased one (1) mm toward a normal or central position and allowed to stay in that position for about 24 hours. Another one (1) mm increment movement is adjusted after each 24 hour period and is repeated until the normal position is reached and stabilized.

Figure 8:
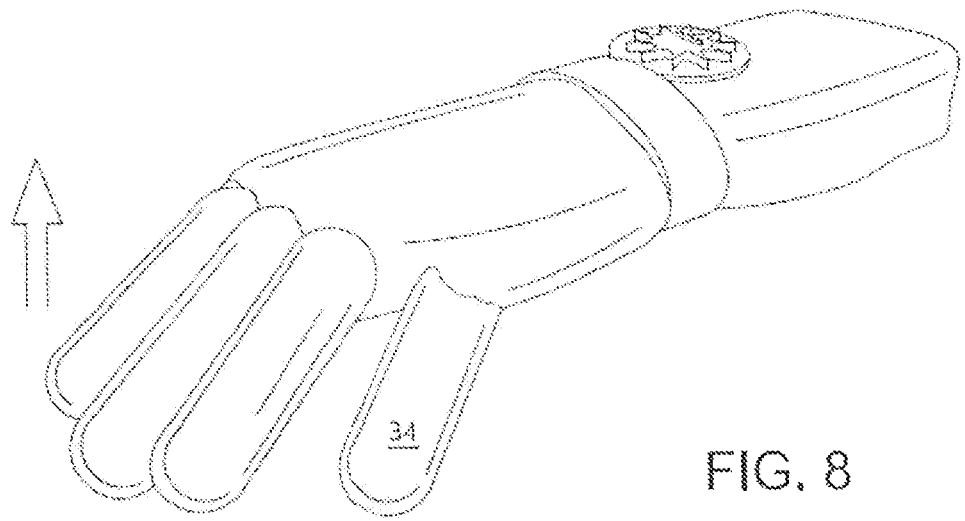
FIG. 8 is a perspective view of an orthopedic device as shown in FIG. 3 with the fingers directed in a downward direction prior to correction.
Figure 9:
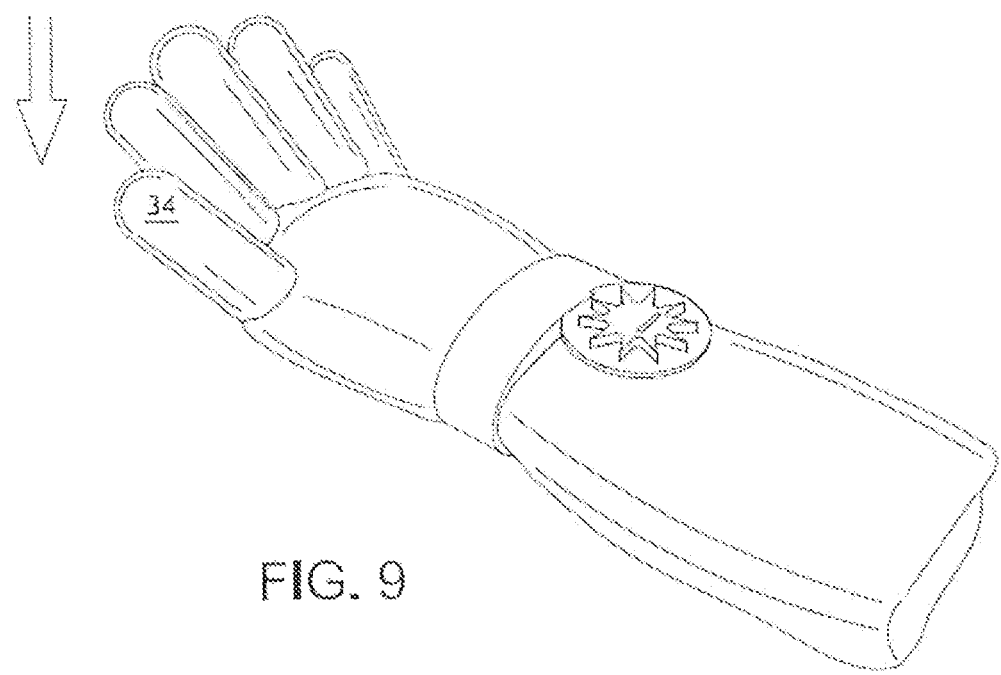
FIG. 9 is a perspective view of an orthopedic device as shown in FIG. 3 but with the fingers oriented in an upward direction before correction.

As illustrated in FIGS. 8 and 9, an abnormality wherein a newborn baby's fingers and thumb are oriented in a downward direction (FIG. 8) or in an upward direction (FIG. 9) is corrected by adjusting a device 20 to fit the baby's fingers and thumb in compartments 30, 31, 32, 33 and 34. The compartments are then moved toward a central or normal position in one (1) mm increments and allowed to remain in each position for 24 hours until the normal position is reached and stable.

The adjustment mechanism 26 preferably has two positions such as an upward position and downward position for making adjustment to the fingers and wherein an upper position of the dial in adjustment mechanism 26 moves the hand with respect to the wrist.

Figure 10:
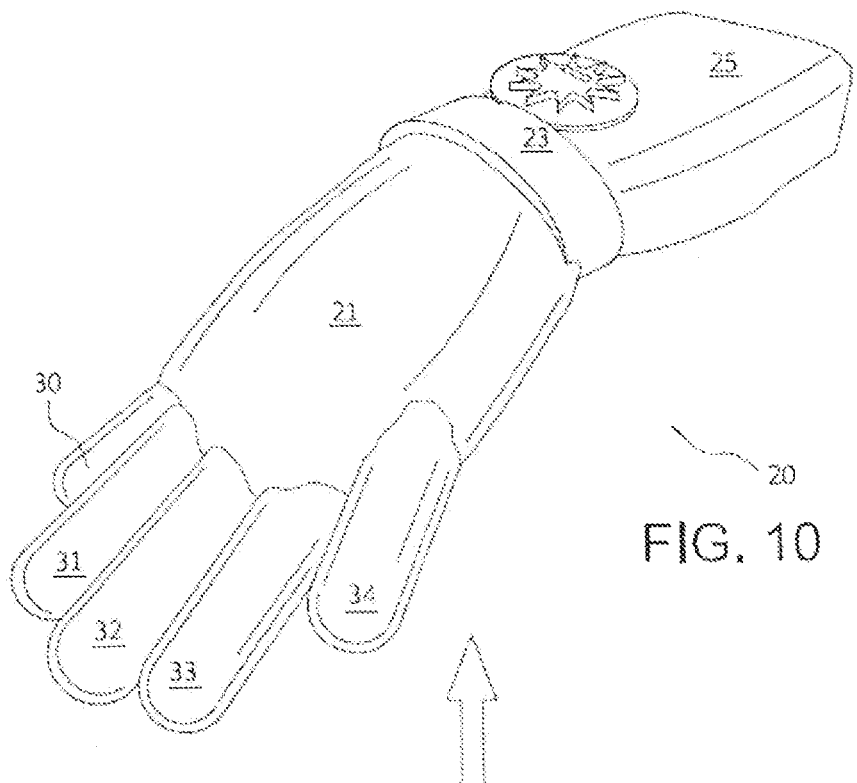
FIG. 10 is a perspective view of an orthopedic device with a hand positioned in a downward direction before correction.
Figure 11:
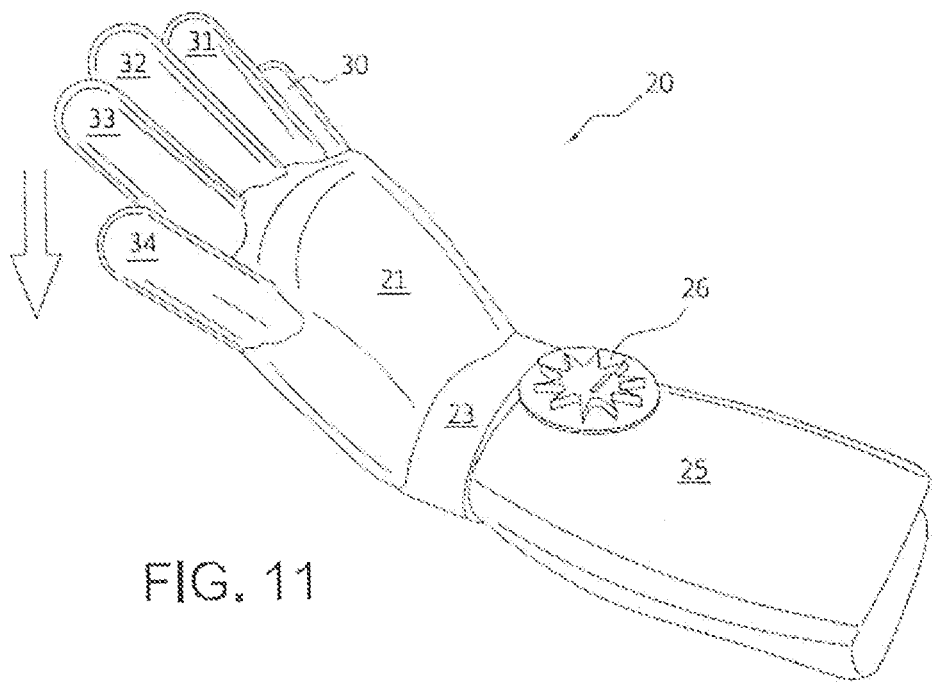
FIG. 11 is a perspective view of an orthopedic device with a hand positioned in an upward direction before correction.

A further embodiment of the invention is illustrated in FIGS. 10 and 11 wherein the hand includes an anomaly when the fingers are properly aligned with the hand of a newborn baby but the hand has an abnormality with respect to the lower long bone. For example, as shown in FIG. 10, an orthopedic device 20 is adjusted to accommodate a new born baby's hand wherein the anomaly relates to a hand that is bent downwardly with respect to the rest of the fingers and thumb that are properly aligned with respect to the hand.

As a result, the baby is fitted with the orthopedic device 20 and the dial or mechanism 26 fitted to the hand inclusive of the abnormality and adjusts the hand upwardly in one (1) mm increment. The correction is biased upwardly by the one (1) mm increments and maintained in each position for 24 hours. The increase in upward movement is repeated by one (1) mm increments per 24 hours until the proper position is reached and held for an additional 24 hours.

The corrections of an abnormality in a newborn baby's hand wherein the hand is positioned upwardly with respect to the wrist and/or lower positioned of a baby's forearm will now be described in connection with FIG. 11. When an abnormality between a newborn baby's hand and wrist result in an upwardly positioned hand an orthopedic device 20 is adjusted to fit the baby's hand and repeated adjustments of one (1) mm increments made with one adjustment per 24 hour period. When the hand is properly aligned and a normal position is stable, no further adjustments are made.

The adjustment mechanism for the above movement should be started as early as possible following the birth of the newborn child and preferably within a few hours of the birth. It is highly desirable to commence treatment within at least ten hours of birth while a baby's bones are still somewhat flexible.

Further adjustment mechanisms are operated in a similar manner to the above.

While the invention has been described in connection with its preferred embodiments, it should be recognized that changes and modifications may be made therein without departing from the scope of the appended claims.

What is claimed is:

1. An orthopedic device for correcting abnormalities in a wrist, hand, fingers and thumb of a newborn baby, said device comprising:
    a glove shaped shell constructed and dimensioned to fit over the wrist, hand and a small portion of the fingers and thumb of a human baby within one (1) to ten (10) hours of the baby's birth;
    a wrist and lower arm engaging portion, a hand engaging portion rotatably connected to said wrist and lower arm engaging portion for rotation upwardly and downwardly, to right and to left and rotatable about a longitudinal axis of a forearm and wrist; and
    an adjustment mechanism for adjusting rotational movements between said wrist and lower arm portion and hand portion in one (1) millimeter increments, wherein said adjustment mechanism includes a planar gear rotatably disposed on said glove shaped shell, a slidable member having a gear slidably disposed at one end thereof and disposed on said glove shaped shell, and wherein said planar gear engages said gear.

2. An orthopedic device for correcting abnormalities in the wrist, hand, fingers and thumb of a newborn baby according to claim 1, in which said glove shaped shell is made of a semi rigid to rigid material.

3. An orthopedic device for correcting abnormalities in the wrist, hand, fingers and thumb of a newborn baby according to claim 1, in which said glove shaped shell is made of a rigid plastic material.

4. An orthopedic device for correcting abnormalities in the wrist, hand, fingers and thumb of a newborn baby according to claim 1, in which said adjustment mechanism includes a first adjustment portion for adjusting movement of the wrist and hand in an upward and downward direction and in a left or right direction and a second adjustment portion independent of said first adjustment portion for adjusting rotation of said hand with respect to a longitudinal axis of said lower arm bone and wrist.

5. An orthopedic device for correcting abnormalities in a wrist, hand, fingers and thumb of a newborn baby consisting of:
- a glove shaped shell constructed and dimensioned to fit over the wrist, hand and at least a small portion of the fingers and thumb of a human baby within one (1) to ten (10) hours of the baby's birth;
- a wrist and lower arm engaging portion, a hand engaging portion rotatably connected to said wrist and a lower arm portion for rotation upwardly and downwardly, to the right and to the left and rotatable about a longitudinal axis of the forearm and wrist; and
- an adjustment mechanism for adjusting said rotational movements between said wrist and lower arm portion and said hand portion in one (1) millimeter increments wherein said adjustment mechanism includes a planar gear rotatably disposed on said glove shaped shell, a slidable member having a gear slidably disposed at one end thereof and disposed on said glove shaped shell, and wherein said planar gear engages said gear.

6. An orthopedic method for correcting skeletal abnormalities in a wrist, hand, fingers and thumb of a newborn human baby, said method comprising the steps of:
- a) providing a glove shaped semi rigid shell member constructed and dimensioned to fit over a newborn baby's wrist, hand, finger and thumb within one (1) to ten (10) hours of the baby's birth and to bias rotational movement of the baby's wrist, hand, fingers and thumb upwardly and downwardly, to the right and to the left and rotationally about a longitudinal axis of a lower arm bone;
- b) adjusting the shell member to fit a baby's wrist, hand, fingers and thumb including an abnormality and to apply a bias toward a normal position;
- c) making further adjustments to increase the bias by an increment of one (1) millimeter and continue each bias for a 24 hour period; and
- d) repeating step c) until the abnormality has been moved to a normal position.

\* \* \* \* \*